US011033290B2

(12) United States Patent
Carrillo, Jr.

(10) Patent No.: US 11,033,290 B2
(45) Date of Patent: Jun. 15, 2021

(54) MEDICAL DEVICE AND METHODS OF USE

(71) Applicant: Boston Scientific Scimed, Inc., Maple Grove, MN (US)

(72) Inventor: Oscar R. Carrillo, Jr., Middletown, CT (US)

(73) Assignee: BOSTON SCIENTIFIC SCIMED, INC, Maple Grove, MN (US)

( * ) Notice: Subject to any disclaimer, the term of this patent is extended or adjusted under 35 U.S.C. 154(b) by 965 days.

(21) Appl. No.: 15/372,954

(22) Filed: Dec. 8, 2016

(65) Prior Publication Data

US 2017/0172602 A1  Jun. 22, 2017

Related U.S. Application Data

(60) Provisional application No. 62/270,249, filed on Dec. 21, 2015.

(51) Int. Cl.
*A61B 17/32* (2006.01)
*A61B 17/3205* (2006.01)
(Continued)

(52) U.S. Cl.
CPC .. *A61B 17/320016* (2013.01); *A61B 1/00089* (2013.01); *A61B 1/00137* (2013.01); *A61B 1/273* (2013.01); *A61B 17/3205* (2013.01); *A61B 17/32053* (2013.01); *A61B 18/1492* (2013.01); *A61M 25/007* (2013.01); *A61M 25/0147* (2013.01); *A61B 2017/00269* (2013.01); *A61B 2017/00818* (2013.01); *A61B 2017/00907* (2013.01);
(Continued)

(58) Field of Classification Search
CPC .... A61B 17/320758; A61B 17/320783; A61B 2017/320791; A61B 2017/320766; A61B 2017/320775; A61B 2018/00202; A61B 2018/00208; A61B 2018/1475
See application file for complete search history.

(56) References Cited

U.S. PATENT DOCUMENTS 2,767,705 A   10/1956 Moore
3,815,604 A * 6/1974 O'Malley ........... A61F 9/00763
                                                        604/22
(Continued)

FOREIGN PATENT DOCUMENTS

JP    2013-541998 A    11/2013

OTHER PUBLICATIONS

International Search Report and Written Opinion mailed in International Application No. PCT/US2016/066062 dated Mar. 1, 2017 (11 pages).
(Continued)

*Primary Examiner* — Ronald Hupczey, Jr.
(74) *Attorney, Agent, or Firm* — Bookoff McAndrews, PLLC

(57) ABSTRACT

The present disclosure is directed to a tissue removal device. The tissue removal device may include a distal portion. The distal portion may include an outer distal portion including a tissue removal tool, and an inner distal portion positioned within the outer distal portion and having a closed distal end, a lumen, and at least one side port, wherein the lumen is configured to receive a medical device, and the inner distal portion is movable relative to the outer distal portion and the medical device.

19 Claims, 12 Drawing Sheets

(51) Int. Cl.
*A61B 1/273* (2006.01)
*A61M 25/01* (2006.01)
*A61M 25/00* (2006.01)
*A61B 1/00* (2006.01)
*A61B 18/14* (2006.01)
*A61B 18/00* (2006.01)
*A61B 17/00* (2006.01)
*A61B 17/30* (2006.01)

(52) U.S. Cl.
CPC ............... *A61B 2017/306* (2013.01); *A61B 2018/00482* (2013.01); *A61B 2018/00488* (2013.01); *A61B 2018/00494* (2013.01); *A61B 2018/00595* (2013.01); *A61B 2018/00982* (2013.01); *A61B 2018/144* (2013.01); *A61B 2018/1412* (2013.01); *A61B 2217/005* (2013.01); *A61B 2217/007* (2013.01); *A61B 2218/007* (2013.01)

(56) References Cited

U.S. PATENT DOCUMENTS

| | | | | |
|---|---|---|---|---|
| 5,507,765 | A * | 4/1996 | Mott | A61B 17/32053 606/184 |
| 5,547,473 | A * | 8/1996 | Peyman | A61F 9/00727 604/22 |
| 5,904,681 | A * | 5/1999 | West, Jr. | A61B 18/1485 604/22 |
| 6,156,049 | A * | 12/2000 | Lovato | A61B 1/015 604/22 |
| 6,193,715 | B1 * | 2/2001 | Wrublewski | A61B 18/1402 604/22 |
| 6,277,135 | B1 * | 8/2001 | Wang | A61B 17/32002 30/316 |
| 6,610,059 | B1 * | 8/2003 | West, Jr. | A61B 17/32002 606/41 |
| 6,986,748 | B2 | 1/2006 | McAlister et al. | |
| 7,169,115 | B2 | 1/2007 | Nobis et al. | |
| 7,658,738 | B2 * | 2/2010 | Nobis | A61B 1/00073 600/105 |
| 8,486,096 | B2 * | 7/2013 | Robertson | A61B 17/3207 606/169 |
| 2004/0249239 | A1 * | 12/2004 | Silverman | A61F 2/04 600/29 |
| 2007/0225734 | A1 | 9/2007 | Bell et al. | |
| 2012/0078038 | A1 * | 3/2012 | Sahney | A61B 1/018 600/104 |
| 2013/0110109 | A1 | 5/2013 | Nguyen et al. | |
| 2014/0027690 | A1 | 1/2014 | Forthman et al. | |
| 2014/0257321 | A1 | 9/2014 | Smith et al. | |
| 2014/0277021 | A1 | 9/2014 | Smith et al. | |
| 2015/0216532 | A1 | 8/2015 | Hlavka et al. | |

OTHER PUBLICATIONS

Japanese Office Action dated Sep. 1, 2020, in counterpart Japanese Patent Application No. 2018-532230 (English translation, 4 pages).

* cited by examiner

MEDICAL DEVICE AND METHODS OF USE

CROSS-REFERENCE TO RELATED APPLICATIONS

This application claims the benefits of priority from U.S. Provisional Application No. 62/270,249, filed on Dec. 21, 2015, the entirety of which is incorporated herein by reference.

TECHNICAL FIELD

The present disclosure relates generally to medical devices. More particularly, the disclosure relates to medical devices used, for example, for dissecting tissue. More particularly, embodiments of the disclosure relate to minimally invasive devices and methods for endoscopic mucosal resection, endoscopic submucosal dissection, and per-oral endoscopic myotomy (POEM). The disclosure also relates to methods of using such devices.

BACKGROUND OF THE DISCLOSURE

Colorectal Cancer is the second leading cause of death in the U.S. There is an unmet need for endoscopic tissue dissection of malignant and pre-malignant lesions. Current treatment options include endoscopic mucosal resection or surgery. Endoscopic resection, done in an outpatient setting, has the potential to dramatically reduce hospital stay as well as morbidity and mortality associated with surgical resection.

When attempting mucosal resection within the GI tract, especially the large intestine, lifting and separating the lesion from the muscularis layer is very challenging. Further, dissecting the ideal amount or layers of tissue may be challenging.

SUMMARY OF THE DISCLOSURE

Aspects of the present disclosure relate to medical devices used for dissecting tissue.

It is to be understood that both the foregoing general description and the following detailed description are exemplary and explanatory only and are not restrictive.

In one example, a tissue removal device may include a distal portion. The distal portion may include an outer distal portion including a tissue removal tool, and an inner distal portion positioned within the outer distal portion and having a closed distal end, a lumen, and at least one side port, wherein the lumen is configured to receive a medical device, and the inner distal portion is movable relative to the outer distal portion and the medical device.

Examples of the medical device may additionally and/or alternatively include one or more other features. Features of the various examples described in the following may be combined unless explicitly stated to the contrary. For example, the at least one side port is configured to apply suction to tissue adjacent to the inner distal portion. The tissue removal device may include the medical device, wherein the distal portion attaches to the medical device. The medical device may be in fluid communication with the lumen of the inner distal portion and the at least one side port. The distal portion may be removably attached to the medical device. The at least one port may include a plurality of ports disposed on between approximately 270 degrees and approximately 90 degrees of a circumference of the inner distal portion. The tissue removal tool may be disposed on between approximately 200 degrees and approximately 90 degrees of a circumference of the outer distal portion. The inner distal portion and the outer distal portion may be positioned so that the tissue removal tool circumferentially aligns with the plurality of ports. The tissue removal device may include a gap between an outer surface of the inner distal portion and the inner surface of the outer distal portion, wherein the radial width of the gap may be between approximately 3 mm and approximately 8 mm. The medical device may be an endoscope. Each of the inner distal portion and the outer distal portion may have a first axial position relative to the medical device and a second axial position relative to the medical device. When in the second axial position, the inner distal portion may be configured to apply suction to a target tissue. The outer distal portion may be configured to dissect the target tissue when the outer distal portion transitions from the first position to the second position. The outer distal portion may be configured to dissect the target tissue when the inner distal portion transitions from the second position to the first position. A distal end of the inner distal portion may be clear.

In another example, a method of dissecting tissue may include inserting a delivery device with a distal portion into a patient, wherein the distal portion includes an inner distal portion and an outer distal portion, the distal portion is external to the delivery device during insertion, and each of the inner distal portion and the outer distal portion is in a first position during insertion, positioning the distal portion proximal to a target tissue, extending the inner distal portion to a second position adjacent the target tissue, applying suction through the delivery device to at least one port disposed in the inner distal portion, and securing the target tissue to the inner distal portion.

Examples of the method of operating the medical device may additionally and/or alternatively include one or more other features. For example, the method may include extending the outer distal portion to a second position, and dissecting the target tissue with a tissue removal tool of the outer distal portion, when the outer distal portion transitions from the first position to the second position. The method may include after securing the target tissue to the inner distal portion, retracting the inner distal portion to the first position, and dissecting the target tissue with a tissue removal tool of the outer distal portion, when the inner distal portion transitions from the second position to the first position. The method may include after securing the target tissue to the inner distal portion, initiating a cautery wire or extending a cutting blade. The distal portion may be removably attached to the medical device. The medical device may be an endoscope.

In another example, a tissue removal device may include a delivery device having an inner lumen extending from a proximal end of the delivery device to a distal end of the delivery device, a distal portion attached an outer surface of to the delivery device. The distal portion may include an outer distal portion including a tissue removal tool, wherein the outer distal portion may be axially movable relative to the delivery device; and an inner distal portion with a closed distal end and at least one side port in fluid communication with the lumen of the delivery device, wherein the inner distal portion may be axially movable relative to the delivery device and the outer distal portion.

Examples of the medical device may additionally and/or alternatively include one or more other features. Features of the various examples described in the following may be combined unless explicitly stated to the contrary. For example, the tissue removal tool may be one of a cautery wire or a cutting blade. When the inner distal portion is in a first position, a proximal-facing wall of the inner distal portion may contacts the distalmost end of the outer distal portion.

BRIEF DESCRIPTION OF THE DRAWINGS

The accompanying drawings, which are incorporated in and constitute a part of this specification, illustrate various examples and together with the description, serve to explain the principles of the disclosure.

DETAILED DESCRIPTION

Reference is now made in detail to examples of the present disclosure, examples of which are illustrated in the accompanying drawings. Wherever possible, the same reference numbers will be used throughout the drawings to refer to the same or like parts. The term "distal" refers to a position farther away from a user end of the device. The term "proximal" refers a position closer to the user end of the device. As used herein, the terms "approximately" and "substantially" indicate a range of values within +/−5% of a stated value.

Aspects of the present disclosure relate to systems and methods for dissecting tissue. The medical devices described herein include a distal portion which is attached to delivery device and may be coaxial with the delivery device. The distal portion includes an inner distal portion and an outer distal portion delivering a radial gap therebetween. The inner distal portion allows for suction to secure tissue to be resected (e.g., target tissue) and the gap between the inner distal portion and the outer distal portion provides a fixed depth resection to reduce the risk of perforation. Additionally, the distal portion may be used with or without injection to lift the tissue, for example a lesion.

It should be noted that the target tissue may be at any location in the body. In some examples, the target tissue may be anywhere within the gastrointestinal (GI) tract including, but not limited to, the large intestine.

Figure 1A:
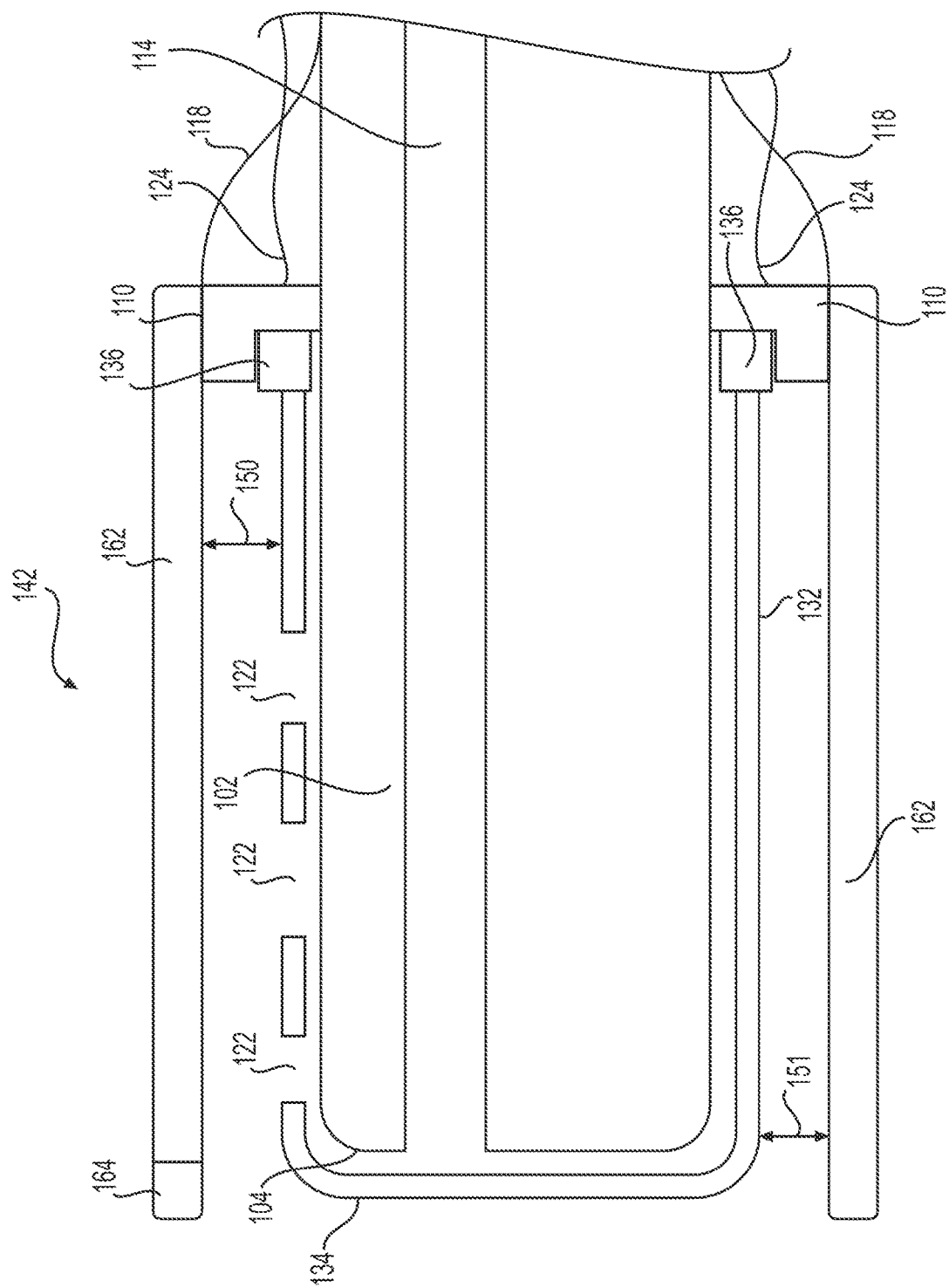
FIGS. 1A and B illustrate a side view and a perspective view of an exemplary delivery device and an exemplary distal portion including an inner distal portion in a first position and an outer distal portion in a first position.
Figure 1B:
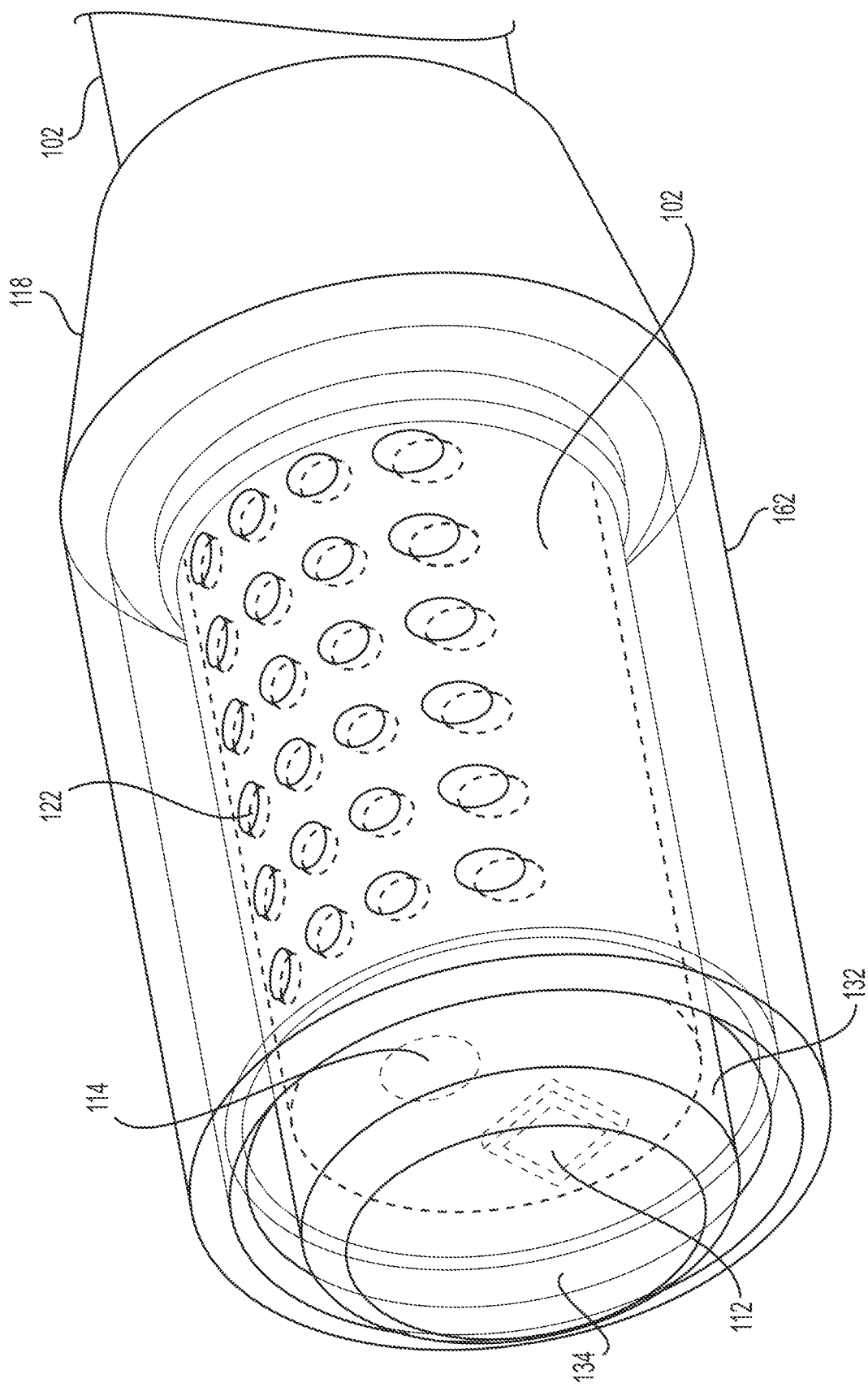

FIGS. 1A and 1B illustrate a distal end of an exemplary medical device for dissecting tissue. The device may include a delivery device 102 and a distal portion 142. Distal portion 142 may include an inner distal portion 132, an outer distal portion 162, a dock 110, and an attachment section 118. Delivery device 102 may either be integral with distal portion 142 or may be coupled to a separate and distinct distal portion 142.

Delivery device 102 may be any device known in the art capable of providing suction to a distal end (e.g., an endoscope, sheath, catheter, ureteroscope, etc.). Delivery device 102 may be used for procedures within or adjacent to various body organs, such as, an esophagus, a heart, a stomach, a pelvic area, a bladder, an intestine, or any other portion of a gastrointestinal, urinary, or pulmonary tract. Delivery device 102 may be configured for insertion into a patient's body through an anatomical opening. In some embodiments, delivery device 102 may be used in natural orifice transluminal endoscopic surgery (NOTES) procedures or single incision laparoscopic surgical (SILS) procedures. Accordingly, delivery device 102 may be shaped and sized for placement into a patient via a body cavity or an incision.

Delivery device 102 includes a proximal end (not shown) and a distal end 104. The proximal end of delivery device 102 may be coupled to a handle portion (not shown). The handle portion and/or the proximal end of delivery device 102 may be attached to a vacuum source, an illumination source, an electrical source, and/or an imaging apparatus.

Figure 2:
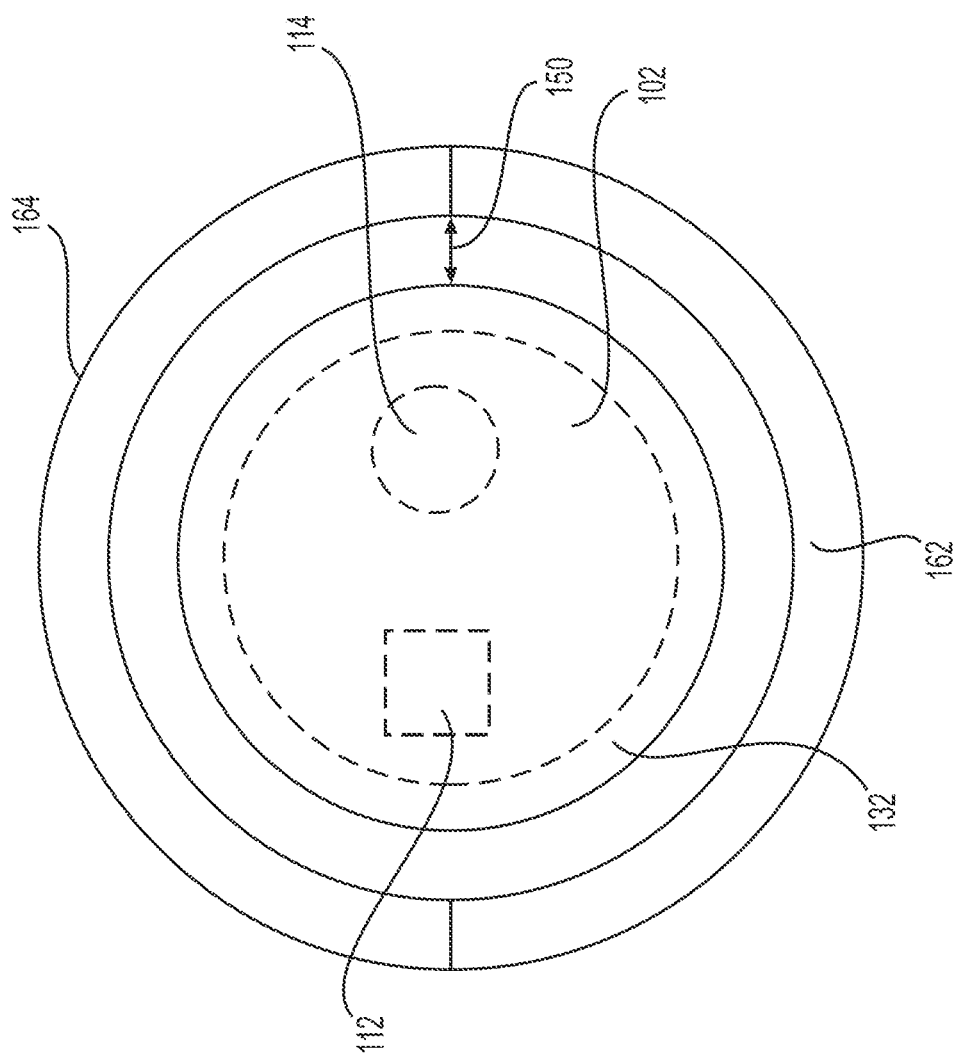
FIG. 2 illustrates a proximal facing view of an exemplary distal end of the medical device of FIGS. 1A and B.

Delivery device 102 may include one or more working channel(s) (e.g., working channel 114 as shown in FIG. 1) extending substantially longitudinally (axially) between the proximal end and the distal end 104 of delivery device 102. In some examples, working channel 114 may be in fluid communication with a vacuum source (e.g., house vacuum, vacuum pump, etc.) to apply suction through working channel 114 to distal end 104 of delivery device 102. The one or more working channels may have any suitable size, cross-sectional area, shape, and/or configuration to, for example, introduce medical instruments (e.g., resection tools) to distal end 104 of delivery device 102 and/or apply suction through distal end 104 of delivery device 102. In some examples, as shown in FIGS. 1B and 2, delivery device 102 may include an imaging/illumination device 112.

As previously mentioned, distal portion 142 may include attachment section 118. FIGS. 1A and 1B illustrate distal portion 142 attached to delivery device 102 via attachment section 118. There may be a fluid tight seal between attachment section 118 and delivery device 102. In some examples, distal portion 142 may be temporarily or permanently attached to delivery device 102. By configuring distal portion 142 to complementarily engage with the distal end of a conventional delivery device (e.g., an endoscope or a catheter), the disclosed device can be used with any existing endoscopes and catheters. A permanently attached distal portion ensures that distal portion 142 does not inadvertently separate from delivery device 102 during a procedure. On the other hand, however, a removably coupled distal portion may allow for utilizing inner and outer distal portions of differing sizes to resect tissue of differing sizes and thicknesses. Based on the desired application, distal portions may be manufactured either permanently attached to delivery device 102 or with attachment means to temporarily attach the distal portion 142 to delivery device 102 having complementary attachment means.

For temporary attachment, the proximal portion of distal portion 142 may include a substantially open attachment section 118, e.g., cylindrical opening for receiving distal end 104 of delivery device 102. In some examples the exterior of attachment section 118 may taper. The taper may be curved (FIG. 1A) or substantially straight (FIG. 1B). The interior of attachment section 118 may include threading, projections, grooves, or any other temporary attachment means for attaching distal portion 142 to complementary structures on the elongate member. Thus, temporary attachments may, for instance, be defined by a screw-fit, Luer taper, snap-fit, or compression fit arrangement. In some embodiments, attachment section 118 may be adjustable, allowing operators to connect elongate members of varying configurations or sizes to distal portion 142. For instance, attachment section 118 may be formed of a flexible material, such as elastic or rubber, which may expand radially to allow distal portion 142 to fit over a range of delivery devices with diameters greater than a diameter of attachment section 118 when attachment section 118 is in a normal state. It will be understood that attachment section 118 can be made from different materials and be configured differently to provide for adjustability without departing from the scope of the present disclosure. Furthermore, mechanisms for holding attachment section 118 to delivery device 102 may be used, including, e.g., hose clamps, wrapped filaments, clips, etc.

Permanent attachment may include welding, gluing, soldering, or other forms of attachment, or distal portion 142 may be integrally formed with delivery device 102. It will be appreciated that other forms of temporary or permanent attachment may be adopted without departing from the scope of the present disclosure. In some embodiments, distal portion 142 may be integral with a sheath which fits along a portion of delivery device 102 from the distal end and proximally. In further examples, this sheath may extend substantially the entire length of delivery device 102.

As previously mentioned, distal portion 142 may include inner distal portion 132, outer distal portion 162, dock 110, and attachment section 118. Dock 110 may connect inner distal portion 132, outer distal portion 162, and attachment section 118. In some examples, dock 110 may contact and/or extend radially outward from an exterior surface of delivery device 102. In some examples, as described in further detail below, dock 110 houses the actuation mechanisms for inner distal portion 132 and outer distal portion 162. FIGS. 1A and 1B illustrate both inner distal portion 132 and outer distal portion 162 in a first position relative to delivery device 102. As shown, in the first position, inner proximal control 136 of inner distal portion 132 may contact a distal-facing wall of dock 110 and a proximal portion (e.g., outer proximal control 137 of FIG. 6) may contact a radially outward facing wall of dock 110.

Inner distal portion 132 and outer distal portion 162 may be generally tubular members configured to be secured to and around distal end 104 of delivery device 102. Inner distal portion 132 may include a closed distal end 134. Outer distal portion 162 may include an open distal end. At least a portion of the distal end of outer distal portion 162 may include a dissection tool 164. Dissection tool 164 will be described in further detail with respect to FIGS. 8 and 9. The proximal ends of inner distal portion 132 and outer distal portion 162 may be releasably connected to dock 110. A proximal end of dock 110 may be coupled to attachment section 118.

Distal portion 142 may be made from any suitable biocompatible material known to one of ordinary skill in the art and having sufficient flexibility to traverse tortuous anatomy. Such materials may include, but are not limited to, rubber, silicon, synthetic plastic, stainless steel, metal-polymer composites, and metal alloys of nickel, titanium, copper cobalt, vanadium, chromium, and iron. In some examples, the material forming portions or all of distal portion 142 may be a superelastic material such as nitinol, which is a nickel-titanium alloy. In some examples, some or all of distal portion 142 may be transparent or translucent. In particular, distal end 134 of inner distal portion 132 (or all of inner distal portion 132) may be transparent (e.g., made of a clear polycarbonate) to provide a clear view for an imaging and/or an illumination device (e.g., imaging/illumination device 112 of FIG. 1B.)

Portions or all of distal portion 142 may be circular, ovoidal, irregular, and/or any shape suitable to enter a body. Further, outer distal portion 162 may have the same shape or a different shape than inner distal portion 132. For example, both may have a substantially circular cross-section and be substantially cylindrical. Portions or all of distal portion 142 may have a uniform shape from proximal end to distal end. In some examples, portions or all of distal portion 142 may have a varying shape, such as a taper at the distal end to facilitate insertion within the body.

Inner distal portion 132 may include a closed distal end 134, a hollow, cylindrical bore, and/or a plurality of side ports 122. The bore of inner distal portion 132 may be in fluid communication with the plurality of side ports 122 and with working channel 114 of delivery device 102. As such, when suction is applied through working channel 114 to distal end 104 of delivery device 102, suction is similarly applied through side ports 122. In some examples, ports 122 may be substantially or at least partially facing radially outward (e.g., the axis of each port 122 may be approximately perpendicular to the longitudinal axis of inner distal portion 132) or ports 122 may be angled toward distal end 134 of inner distal portion 132 so suction is applied toward the distal end of the medical device. The angling of suction applied through ports 122 may also include angling the passage(s) (e.g., branches extending from the interior of inner distal portion 132 to exterior of inner distal portion 132) connected to ports 122. The angle of ports 122 may be greater than approximately 10 degrees from the longitudinal axis of inner distal portion 132 to less than approximately 90 degrees from the longitudinal axis of inner distal portion 132, preferably between approximately 20 degrees and approximately 80 degrees. Angling the application of suction toward the distal end 134 of inner distal portion 132 may assist in securing target tissue located distally of inner distal portion 132.

There may be any number of side ports 122, spaced any distance apart, and located anywhere along the radial surface of inner distal portion 132. The plurality of ports may include any numbers of rows or columns. In some examples, inner distal portion 132 includes linear, evenly dispersed rows of side ports 122 extending circumferentially about inner distal portion 132, e.g., six evenly spaced rows as illustrated in FIG. 1B. In the examples illustrated herein, the rows are substantially linear, but the plurality of ports are not limited thereto and may be in any pattern. In some examples, each row includes any number of ports. In some examples, each row may include the same number of ports or each row may include a different number of ports than other row(s). For example, FIG. 1B shows four longitudinally arranged columns. In some examples, the density of ports 122 may vary, e.g., ports may be closer together at the distal end than the proximal end or vice versa.

Ports 122 may be disposed on any portion of the circumference of inner distal portion 132. For example, the ports may be located on an entire 360 degrees of the circumference of inner distal portion 132. In other examples, like those illustrated herein, ports 122 may be disposed on between approximately 270 degrees and approximately 90 degrees, or approximately 180 degrees and approximately 120 degrees of the circumference of inner distal portion 132. In some examples, ports 122 may be disposed on less than approximately 180 degrees. Ports 122 may only be on a portion (e.g., less than 360 degrees) of the outer surface, so that ports 122 may be positioned at or near target tissue and only pull target tissue toward inner distal portion 132.

The side ports 122 may be any size and/or shape. The size and/or shape of ports 122 may depend on the size and/or type of target tissue. For example, the ports should be large enough to suction at least some of the target tissue into the port to provide traction. Conversely, the ports 122 should not be too large (and the suction force should not be so strong) as to suction in so much tissue as to inadvertently dissect deeper layers of tissue. Ports 122 may be substantially circular and may have a diameter of approximately 2-4 millimeters. In some examples, each of the plurality of ports 122 may have substantially the same diameter. In some examples, the diameter of each of port 122 may vary.

Distal portion 142 may have any length, cross-sectional shape and/or configuration and may be any desired dimension that can be received in a body cavity, connect to delivery device 102, and dissect the target tissue. For example, both inner distal portion 132 and outer distal portion 162 may have the same or different length. The length of inner distal portion 132 and outer distal portion 162 may be between approximately 15 mm and approximately 30 mm, or between approximately 20 mm and approximately 25 mm. In some examples, the inner diameter of inner distal portion 132 may be sized to surround and slide over delivery device 102. The gap between the inner distal portion 132 and delivery device 102 may be any size capable of allowing inner distal portion 132 to slide relative to delivery device 102 in the longitudinal direction. In some examples, the outer diameter of inner distal portion 132 may be approximately 10 mm to approximately 15 mm, or approximately 12.5 mm. The inner diameter of outer distal portion 162 may be sized to surround and slide over inner distal portion 132. As illustrated FIG. 1A, there may be a gap 150 between a portion of inner distal portion 132 (e.g., the portion with side ports 122) and the outer distal portion 162. Another sized gap 151 may be between another portion of inner distal portion 132 (e.g., a portion without side ports 122) and the outer distal portion 162. In some examples, the gap between inner distal portion 132 and outer distal portion 162 may be substantially constant (e.g., gap 150 and gap 151 are substantially the same forming an annular gap between inner distal portion 132 and outer distal portion 162). In other examples, gap 151 is smaller than gap 150 (e.g., because gap 150 is configured to receive dissected tissue and gap 151 is not). For example, an off-axis inner distal portion 132 (e.g., the axis of inner distal portion 132 is not coincident with the axis of outer distal portion 162) may maximize gap 150 and thus achieve a maximum dissected/resected tissue thickness. In some examples, the circumference of distal portion 142 associated with gap 150 and gap 151 may be defined by dissection tool 164. For example, gap 150 may be between inner distal portion 132 and a circumferential portion of outer distal portion 162 (e.g., the portion with dissection tool 164) and gap 151 may be between inner distal portion 132 and another circumferential portion of outer distal portion 162 (e.g., the portion without dissection tool 164). Gap 150 may have any radial width (e.g., the space between the outer surface of inner distal portion 132 and the inner surface of outer distal portion 162). For example, gap 150 may be between approximately 2 mm and approximately 9 mm in radial width, or between approximately 3 mm and approximately 8 mm, or approximately 5 mm. The radial width of gap 150 may depend on the target tissue. For example, the target tissue (e.g., the tissue desired for dissection) in the esophagus may be thicker than target tissue within the colon or duodenum. For a distal portion (e.g., distal portion 142) designed for dissection within the esophagus, gap 150 may be between approximately 6 mm and approximately 10 mm, or approximately 8 mm. In examples in which distal portion 142 is designed for dissection within the colon or duodenum, gap 150 may be between approximately 2 mm and approximately 4 mm, or approximately 3 mm.

FIG. 2 illustrates a proximal-facing view of the distal end of the medical device. As shown, delivery device 102, including working channel 114 and imaging/illumination device 112, is disposed with inner distal portion 132. Gap 150 separates inner distal portion 132 and outer distal portion 162. A portion (e.g., a cutting arc length) of the circumference of outer distal portion 162 includes dissection tool 164. For example, the dissection tool 164 may extend an entire 360 degrees of the circumference of outer distal portion 162. In other examples, like those illustrated herein, dissection tool 164 may be disposed on between approximately 200 degrees and approximately 90 degrees, or approximately 180 degrees and approximately 120 degrees of the circumference of outer distal portion 162. In some examples, dissection tool 164 may be disposed on approximately 180 degrees (as shown in FIG. 2). Exemplary dissection tools and their configuration within outer distal portion 162 are described in further detail below with respect to FIGS. 8 and 9.

Figure 3A:
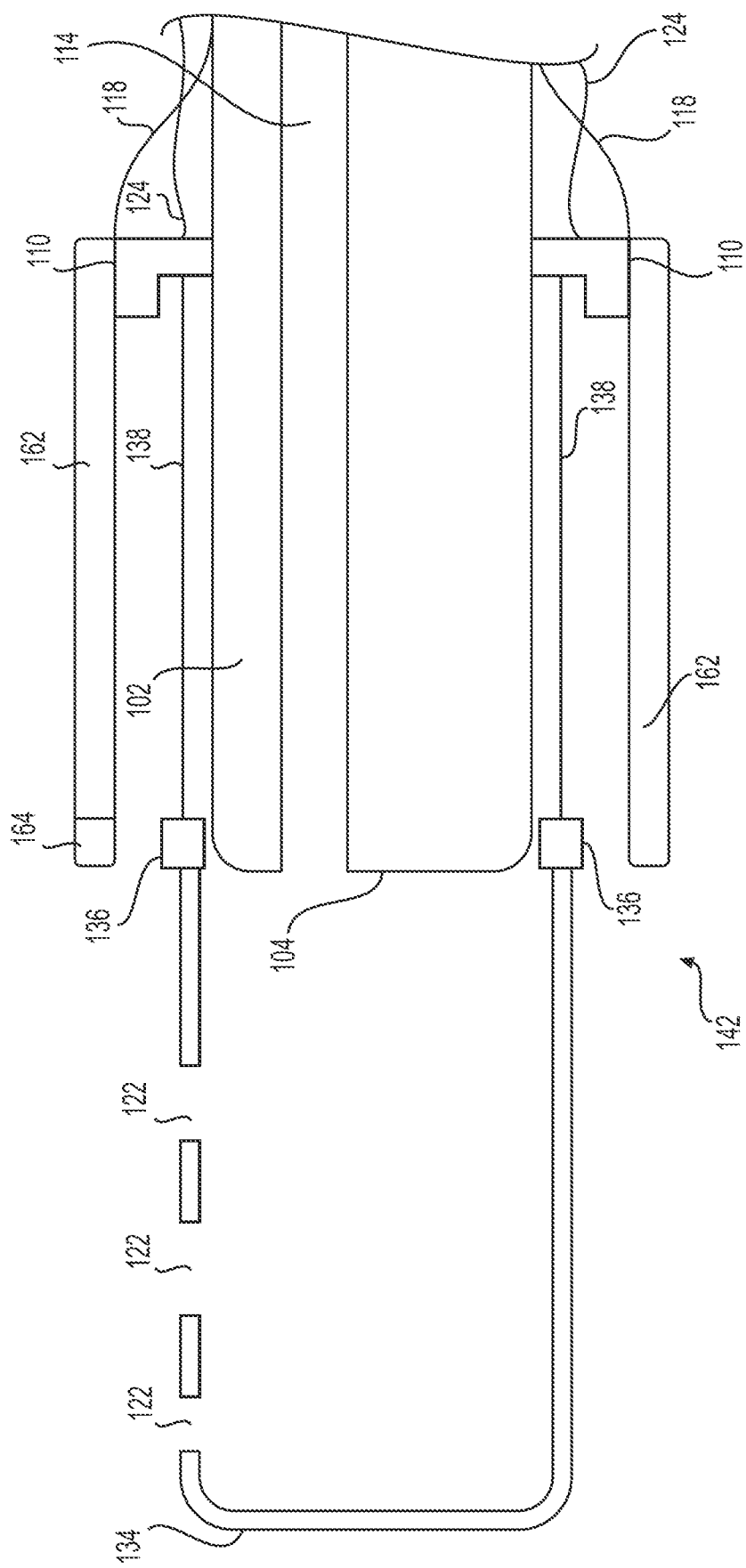
FIGS. 3A and 3B illustrate a side view and a perspective view of the medical device of FIGS. 1A and B in which the inner distal portion is in a second position and the outer distal portion is in the first position.
Figure 3B:
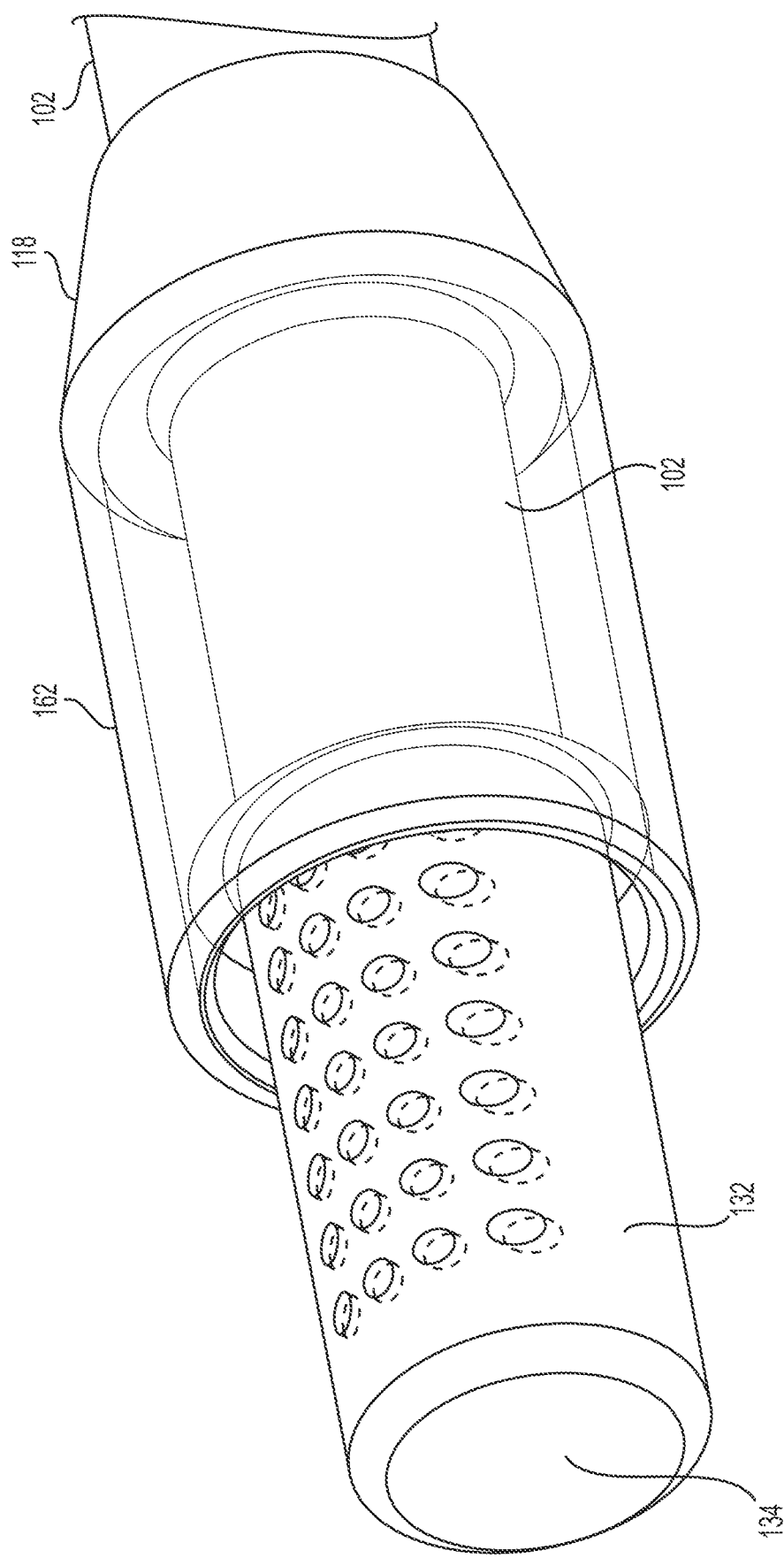

Distal portion 142 may enter a patient with both inner distal portion 132 and outer distal portion 162 in the first position relative to delivery device 102. Distal portion 142 may be placed just proximal of the target tissue and/or distal portion 142 (or only inner distal portion 132) may be rotated so that side ports 122 face the target tissue. Once in this orientation, inner distal portion 132 may be moved distally, to a second position so that side ports 122 are adjacent to the target tissue. FIGS. 3A and 3B illustrate a side view and a perspective view of the medical device with inner distal portion 132 in a second position relative to delivery device 102 and outer distal portion 162 in a first position relative to delivery device 102. The proximalmost end of inner distal portion 132 may not move beyond a distalmost end of delivery device 102. Inner distal portion 132 and deliver device 102 may form a fluid tight seal (e.g., between inner proximal control 136 and an outer surface of delivery device 102). Inner distal portion 132 may be moved in any way known in the art. In some examples, a pull/push mechanism may be used. Such mechanisms may be one or more pull wires, and/or single or multiple rod. In some examples, the actuation mechanism, may be actuation mechanism 138. Actuation mechanism 138 is disposed external to delivery device 102. In the example shown in FIG. 3A, actuation mechanism 138 extends between dock 110 and inner proximal control 136. In some examples, an actuation mechanism may be disposed within delivery device 102. The actuation mechanism may extend through a working channel of delivery device 102, e.g., working channel 114.

Figure 4:
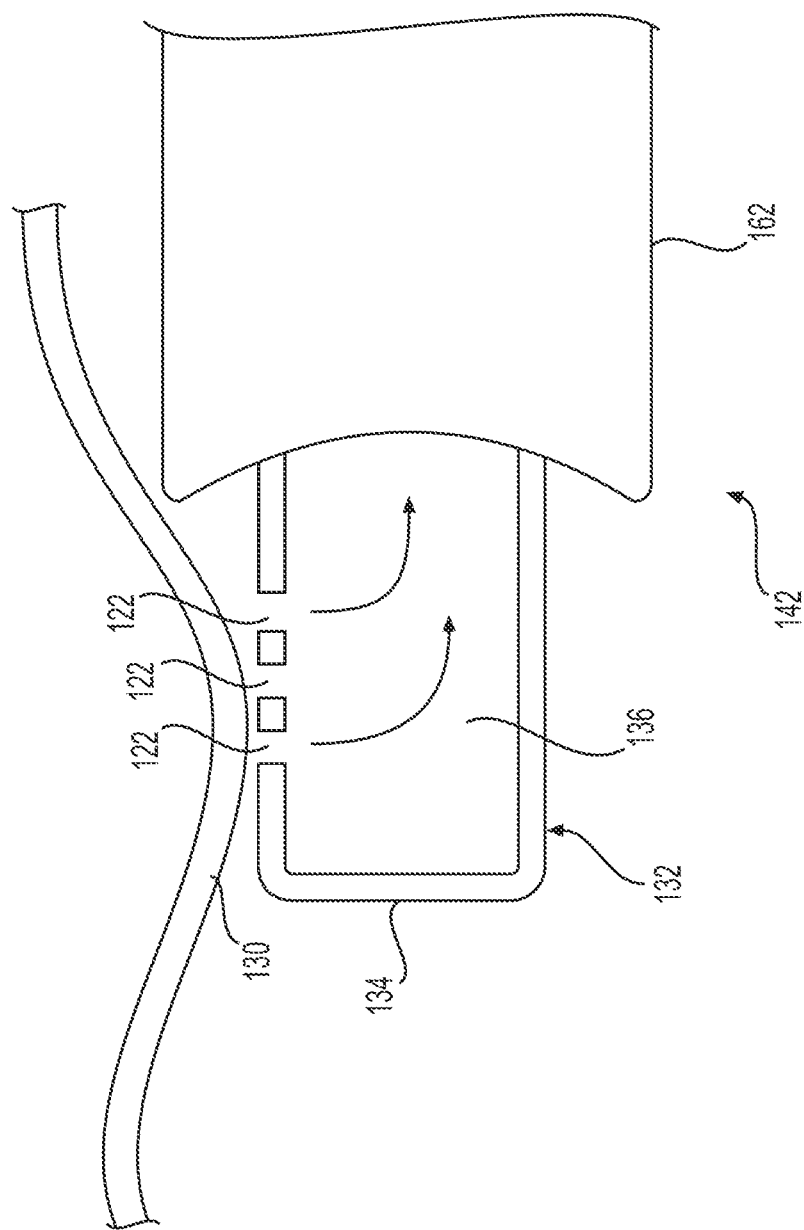
FIG. 4 illustrates a side view of the medical device when suction is applied to target tissue through the inner distal portion in the second position and with the outer distal portion in the first position.

FIG. 4 illustrates a side view of distal portion 142 applying suction to target tissue 130. In this example, distal portion 142 may have first been positioned proximal of target tissue 130. Inner distal portion 132 was moved so that side ports 122 aligned with target tissue 130. Once in such a position, an operator may initiate a vacuum source to apply suction through e.g., working channel 114 of delivery 102. This suction may then be applied to target tissue 130 through side ports 122 of inner distal portion 132. The rate of suction may depend on the size and/or type of target tissue. For example, the suction may be of sufficient force to pull at least some of the target tissue into the port to provide traction. Conversely, the suction should not be too large as to pull in so much tissue as to inadvertently dissect deeper layers of tissue. In some examples, the rate of suction may be between approximately 575 millibar to approximately 850 millibar.

Figure 5:
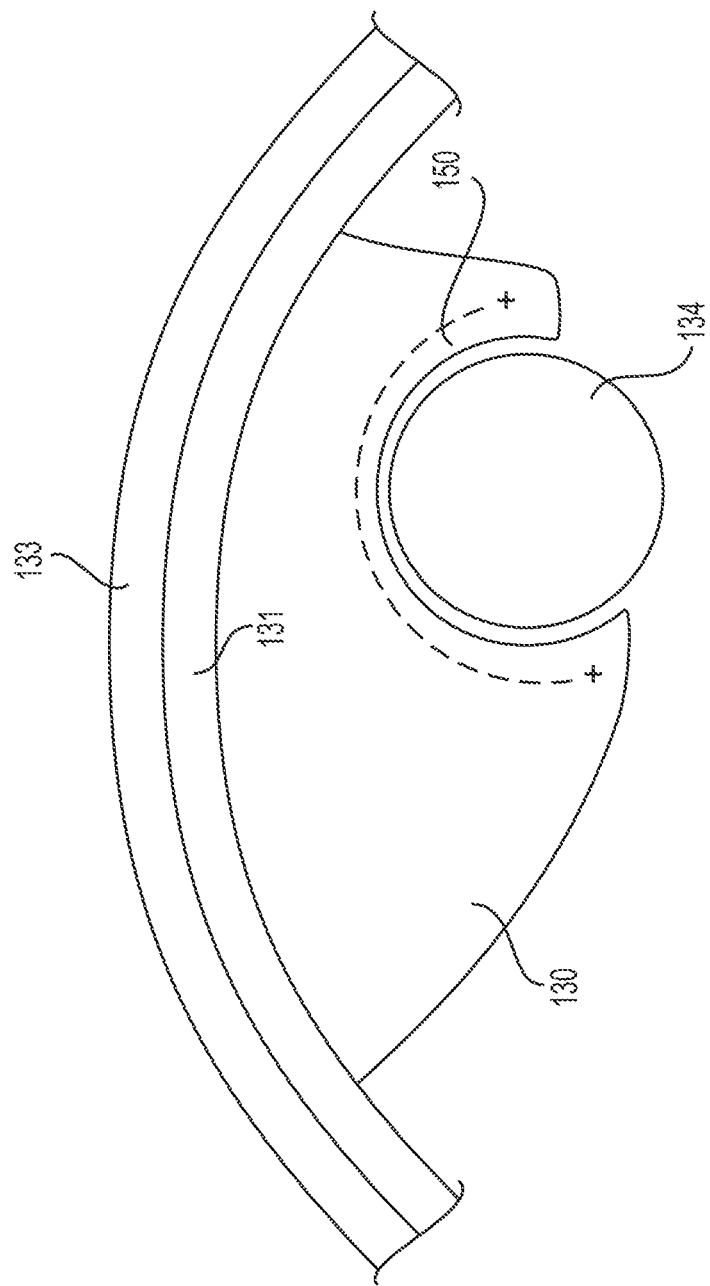
FIG. 5 illustrates a proximal-facing view of an exemplary distal end of an exemplary inner distal portion with target tissue pulled by suction around the inner distal portion.

FIG. 5 illustrates a proximal-facing view of distal end 134 of inner distal portion 132 with target tissue 130 pull around a circumferential portion of inner distal portion 132 via suction. Layer 131 illustrates a deeper tissue layer than target tissue 130. An operator may wish to avoid dissecting deeper layer 131. By setting outer distal portion 162 (and thus dissection tool 164) a certain distance (e.g., the radial width of gap 150) away from inner distal portion 132, the cross-sectional width of the dissected tissue may be limited to the radial width of gap 150, as illustrated by the dotted line of FIG. 5. An operator may choose a distal portion 142 and/or gap 150 to ensure that the radial width of gap 150 does not exceed the cross-sectional width of the layer of tissue desired for dissected and thus, may avoid dissection deeper layers.

Figure 6:
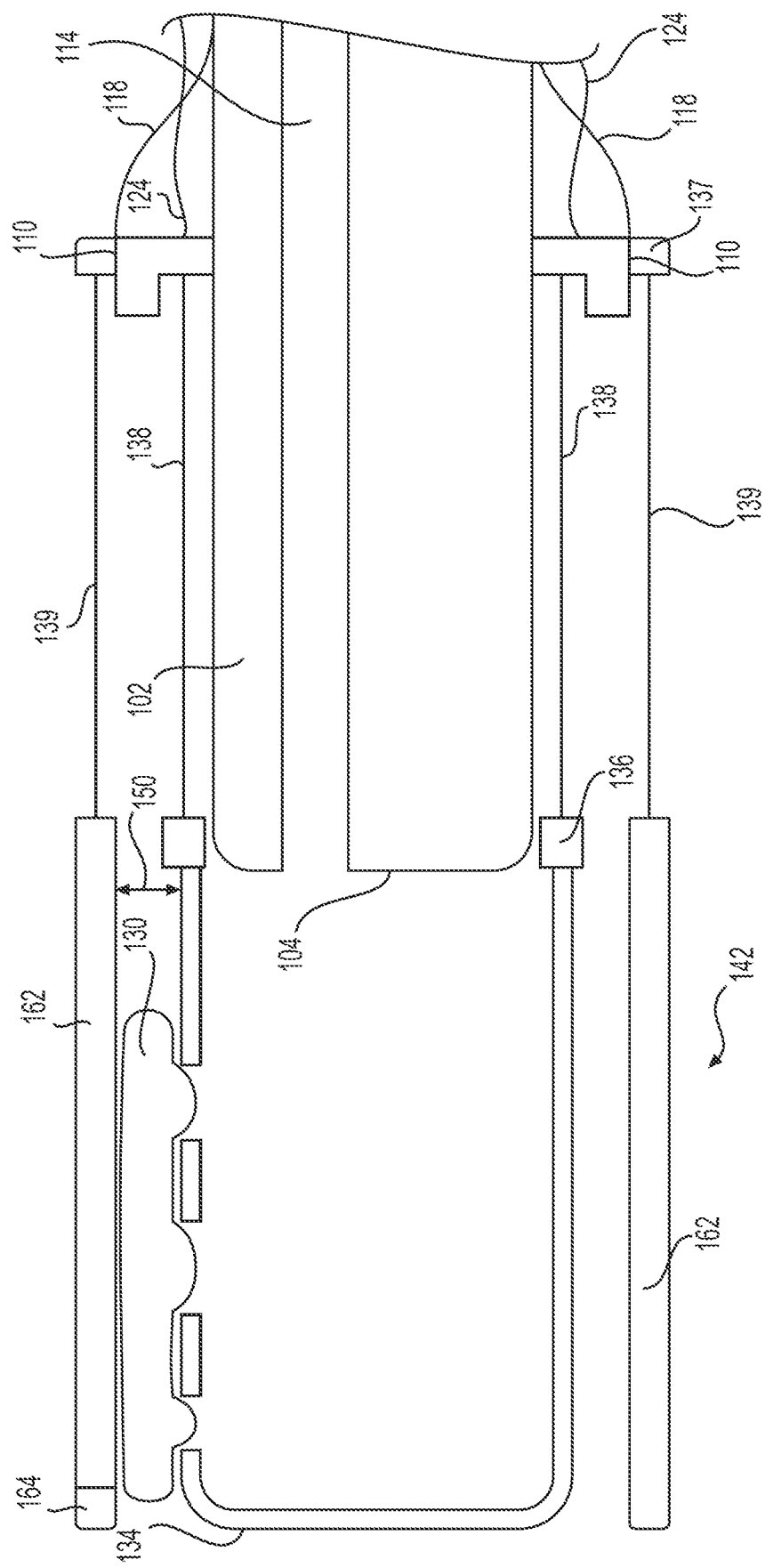
FIG. 6 illustrates a side view of an exemplary delivery device and an exemplary distal portion including an inner distal portion in a second position and an outer distal portion in a second position.
Figure 7:
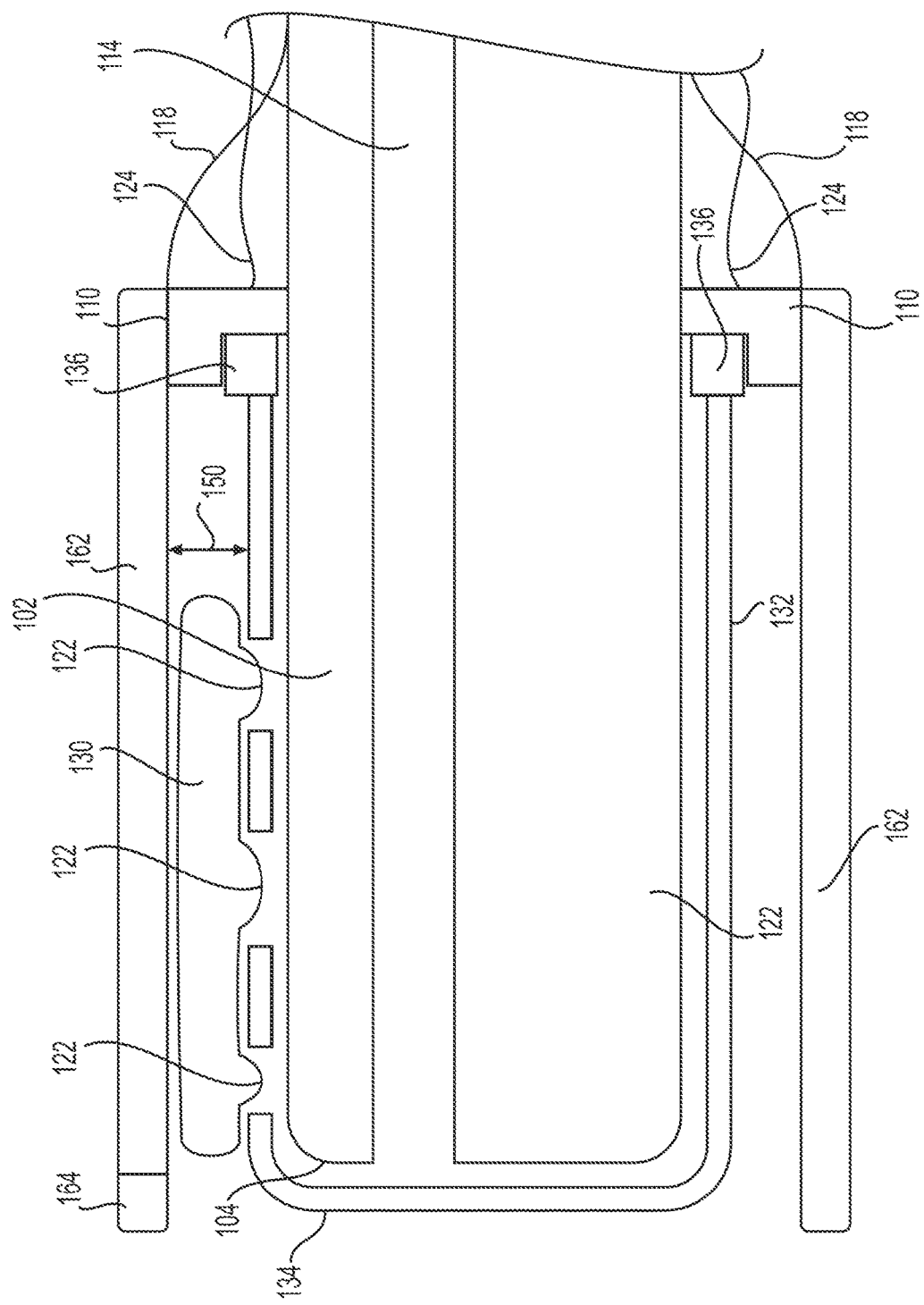
FIG. 7 illustrates a side view of an exemplary delivery device and an exemplary distal portion after dissection with the inner distal portion in the first position and the outer distal portion in the first position.

FIGS. 6 and 7 illustrate exemplary alternative methods of dissecting target tissue 130 with distal portion 142. In the example illustrated in FIG. 6, both inner distal portion 132 and outer distal portion 162 are in the second position relative to delivery device 102. Once securing target tissue 130 (e.g., as shown in FIG. 4) to inner distal portion 132, outer distal portion 162 may be moved distally. Outer distal portion 162 may be moved in any way known in the art. In some examples, a pull/push mechanism may be used. Such a mechanism may be one or more pull wires, and/or single or multiple rod. In some examples, the actuation mechanism may be actuation mechanism 139. Actuation mechanism 139 is disposed external to delivery device 102. In the example shown in FIG. 6, actuation mechanism 139 extends between outer proximal control 137 (affixed to a radially outward facing wall of dock 110) and a proximalmost end of outer distal portion 162. In some examples, an actuation mechanism may be disposed within delivery device 102. The actuation mechanism may extend through a working channel of delivery device 102, e.g., working channel 114. Dissection tool 164 may slice the target tissue 130 as outer distal portion 162 moves distally through the target tissue. Dissection tool 164 may be used to dissect and collect a portion of tissue 130 into gap 150.

In the example illustrated in FIG. 7, both inner distal portion 132 and outer distal portion 162 are in the first position relative to delivery device 102. Once securing target tissue 130 (e.g., as shown in FIG. 4) to inner distal portion 132, inner distal portion 132 may be moved proximally, pulling portions of the target tissue proximally as well. In some examples, a higher amount of suction may need to be applied when using such a method. Inner distal portion 132 may be moved in any way known in the art, including those described above. Dissection tool 164 may slice the target tissue 130 as inner distal portion 132 moves proximally and pulls target tissue 130 through dissection tool 164. Dissection tool 164 may be used to dissect a portion of 130 tissue and collect the dissected tissue in gap 150. In examples in which this method is used, distal portion 142 may be designed so that outer distal portion 162 is fixed relative to delivery device 102 and unable to move distally as shown in FIG. 6. In some examples, outer distal portion 162 is capable of moving distally as shown in FIG. 6, and, as appropriate, an operator may choose between the method illustrated in FIG. 6, the method illustrated in FIG. 7, and a combination thereof. When dissecting, at least a portion of ports 122 of inner distal portion 132 are aligned with the cutting arc (e.g., the portion of outer distal portion 162 including dissection tool 164). In some examples, all of the plurality of ports 122 are within the cutting arc.

Figure 8:
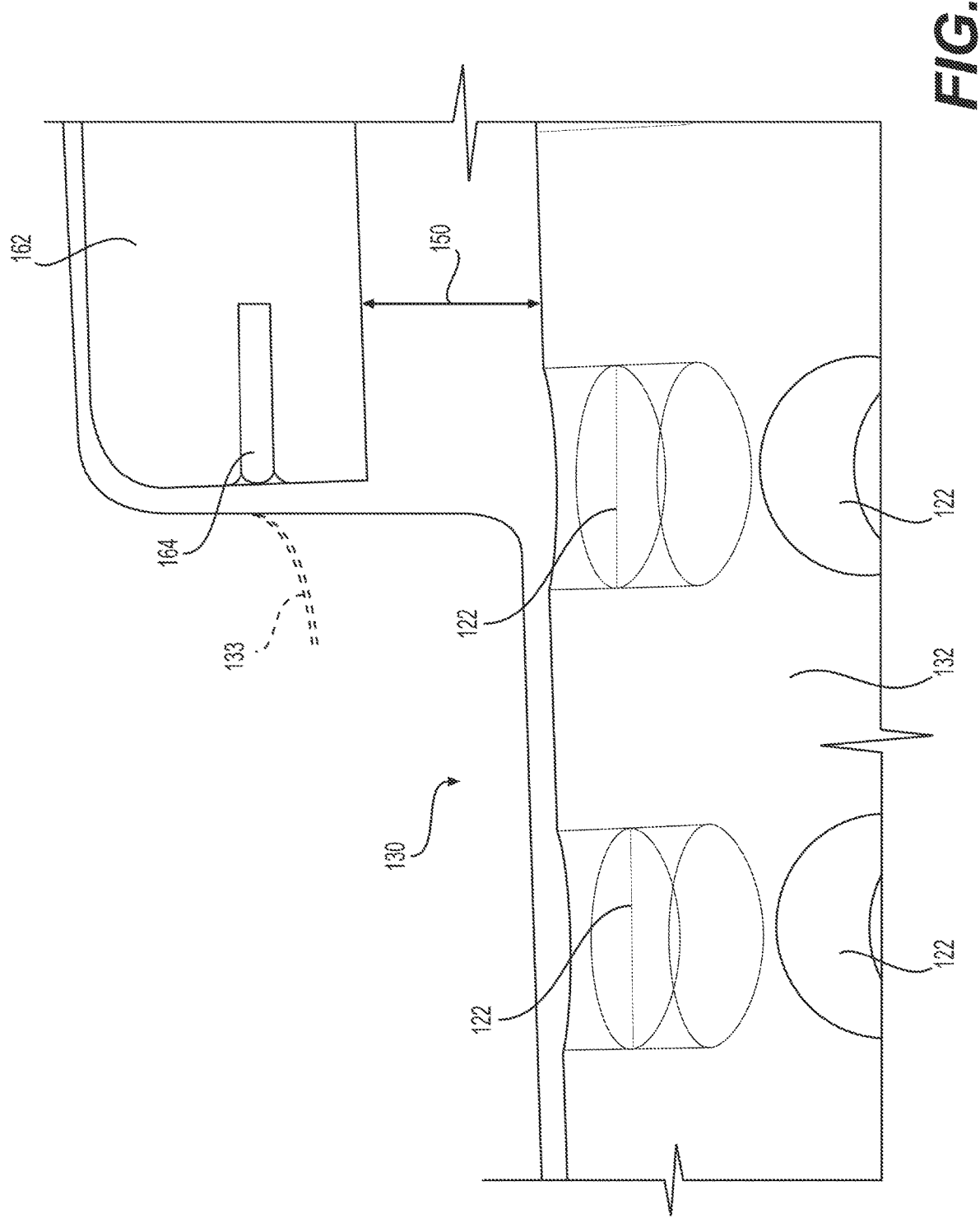
FIG. 8 illustrates an exemplary distal portion with an exemplary dissection tool.
Figure 9:
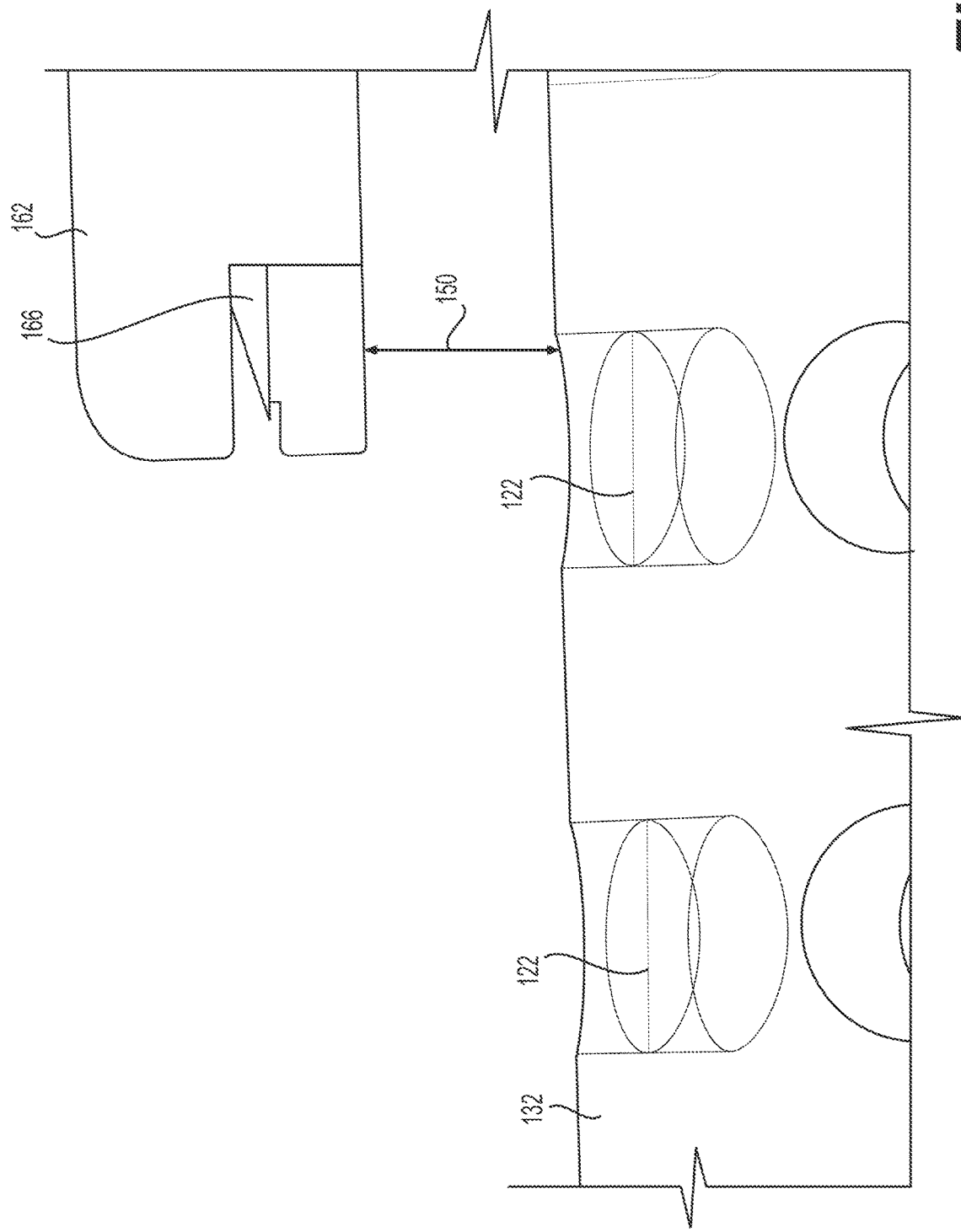
FIG. 9 illustrates an exemplary distal portion with an alternative exemplary dissection tool.

FIGS. 8 and 9 illustrate two exemplary dissection tools embedded with a portion of the circumference of outer distal portion 162. FIG. 8 illustrates a cautery wire 164 embedded within outer distal portion 162. The wire 164 may remain off or "cold" during insertion and positioning of inner distal portion 132 and outer distal portion 162. Once ready for dissection, the operator may initiate electricity to travel through a wire (e.g., wire 124 of FIG. 1) from the proximal end of the delivery device to the cautery wire 164. As inner distal portion 132 moves target tissue 130 toward wire 164 and/or outer distal portion 162 moves wire 164 toward target tissue 130, the "hot" cautery wire 164 may cut through target tissue 130 at cut line 133.

FIG. 9 illustrates a retractable cutting blade 166 embedded within outer distal portion 162. In some examples, the cutting blade 166 may have a curved of semi-circular shape so as to be disposed along the entire cutting arc length of the circumference of outer distal portion 162. The cutting blade 166 may remain retracted during insertion and positioning of distal portion 142. Once ready for dissection, the operator may push the retractable blade 166 out of its housing/cavity. As inner distal portion 132 moves target tissue 130 toward cutting blade 166 and/or outer distal portion 162 moves cutting blade 166 toward target tissue 130, the extended cutting blade 166 may cut through the target tissue.

In some examples, inner distal portion 132 may be capable of axial rotation. In such examples, a first sample of target tissue may be resected, and then inner distal portion 132 may rotate, for example, 180 degrees or less, to deposit the first tissue sample in an unused space opposite side ports 122. Inner distal portion 132 may then rotate, for example 180 degrees or less to resect a second tissue sample. In some examples, small dissection tools may oscillate back and forth across the cutting arc length instead of one dissection tool extending the entire cutting arc length.

Figure 10:
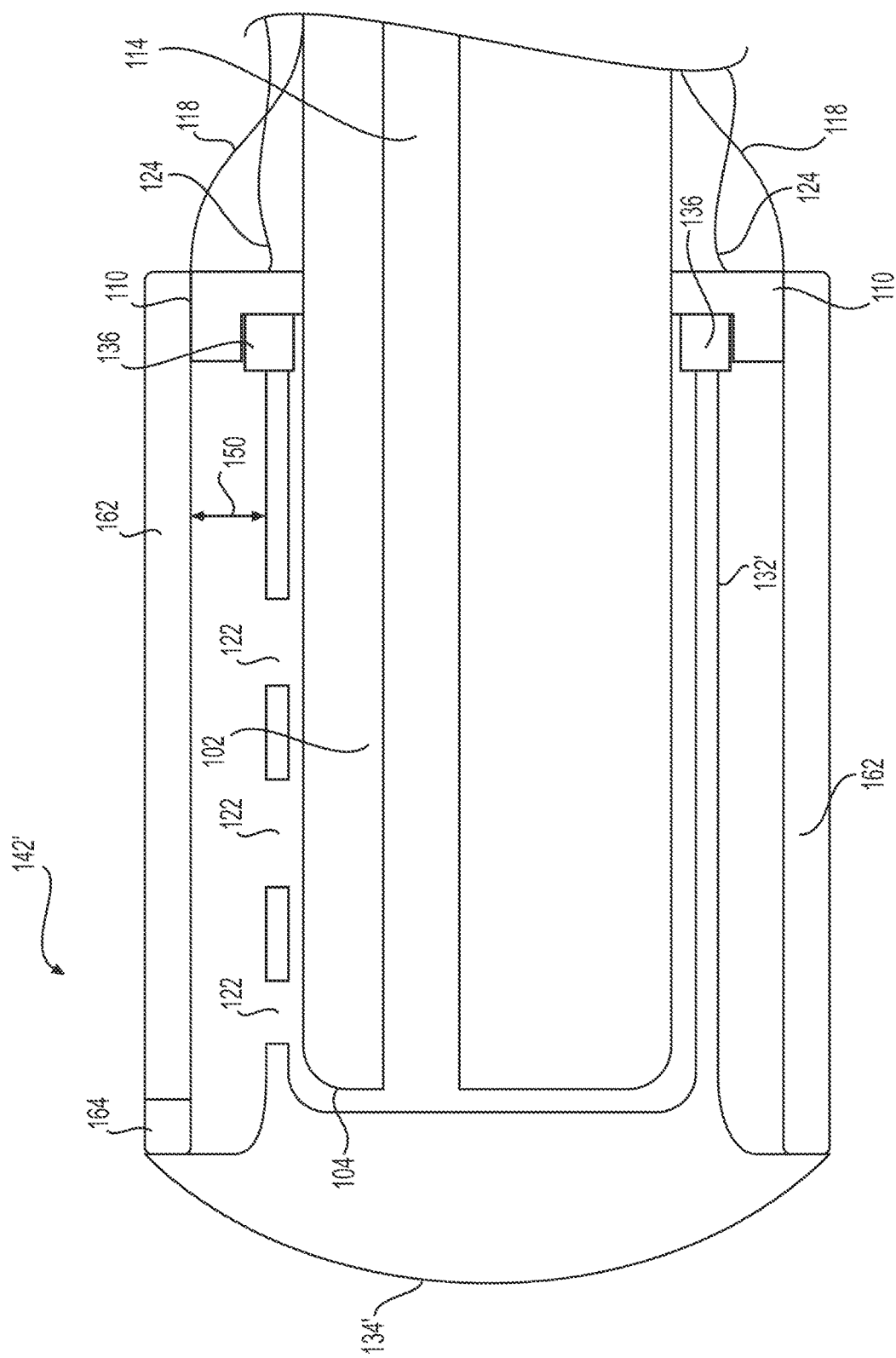
FIG. 10 illustrates a side view of an alternative exemplary distal portion.

FIG. 10 illustrates an alternative exemplary distal portion 142' including inner distal portion 132'. In some examples, distal end 134' of inner distal portion 132' may extend distally and radially outward so as to contact the distalmost ends of outer distal portion 162. In such examples, dissection tool 164 (such as blade 166) may not need to be retracted within outer distal portion 162. For example, a cutting blade may be positioned on the distalmost end of outer distal portion 162. Such a cutting blade need not be retractable as distal end 134' of inner distal portion 132' may provide protection to the patient from the cutting blade during insertion and positioning of distal portion 142.

In some examples, target tissue may be secured to inner distal portion 132 in any way known in the art. For example, hooks may be disposed on the exterior of inner distal portion 132. In other examples, inner distal portion 132 may include at least one hole large enough to provide a grasper access to tissue and to pull the tissue into inner distal portion 132. These graspers may extend from a proximal end of delivery device 102, through a working channel (e.g., working channel 114), to the "larger" hole(s) in inner distal portion 132. Further, inner distal portion 132 may include an internal ramp to facilitate these graspers access to the target tissue.

The many features of the disclosure are apparent from the detailed specification, and thus, it is intended by the appended claims to cover all such features of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other aspects of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A tissue removal device, comprising:
   a distal portion, comprising:
      an outer distal portion including an outer lumen and a tissue removal tool configured to sever tissue, wherein the tissue removal tool is positioned about a full circumference of the outer distal portion and external of the outer lumen, the tissue removal tool is movable relative to portions of the outer distal portion proximate to the tissue removal tool;
      an inner distal portion positioned within the outer lumen of the outer distal portion and having a closed distal end, a lumen, and at least one side port, wherein the lumen is configured to receive a medical device, and the inner distal portion is movable relative to the outer distal portion and the medical device; and
      a gap between an outer surface of the inner distal portion and an inner surface of the outer distal portion.

2. The tissue removal device of claim 1, wherein the at least one side port is configured to apply suction to tissue adjacent to the inner distal portion.

3. The tissue removal device of claim 1, further comprising the medical device, wherein the distal portion attaches to the medical device.

4. The tissue removal device of claim 3, wherein the medical device is in fluid communication with the lumen of the inner distal portion and the at least one side port.

5. The tissue removal device of claim 4, wherein the distal portion is removably attached to the medical device.

6. The tissue removal device of claim 1, wherein the at least one side port includes a plurality of ports disposed on between approximately 270 degrees and approximately 90 degrees of a circumference of the inner distal portion.

7. The tissue removal device of claim 1, wherein the tissue removal tool is disposed within a cavity formed along a distal edge of the outer distal portion.

8. The tissue removal device of claim 6, wherein the inner distal portion and the outer distal portion are positioned so that the tissue removal tool circumferentially aligns with the plurality of ports.

9. The tissue removal device of claim 1, wherein the radial width of the gap is between approximately 3 mm and approximately 8 mm.

10. The tissue removal device of claim 1, wherein the medical device is an endoscope, and the tissue removal tool is a retractable cutting blade.

11. A tissue removal device, comprising:
    a delivery device having an inner lumen extending from a proximal end of the delivery device to a distal end of the delivery device, wherein the delivery device is an endoscope;
    a distal portion attached to an outer surface of the delivery device, the distal portion defining a longitudinal axis and comprising:
       an outer distal portion including a tissue removal tool configured to sever tissue, wherein the outer distal portion is axially movable relative to the delivery device, and the tissue removal tool is positioned along a distal edge of the outer distal portion; and
       an inner distal portion with a closed distal end and at least one side port in fluid communication with the lumen of the delivery device, wherein the inner distal portion is axially movable relative to the delivery device and the outer distal portion, wherein the at least one side port is angled relative to the longitudinal axis and in a distal direction toward the closed distal end.

12. The tissue removal device of claim 11, wherein the tissue removal tool is one of a cautery wire or a cutting blade.

13. The tissue removal device of claim 12, wherein, when the inner distal portion is in a first position, a proximal-facing wall of the inner distal portion contacts a distalmost end of the outer distal portion.

14. A tissue removal device, comprising:
    a distal portion, comprising:
       an inner distal portion including at least one side port and an inner lumen configured to receive a medical device; and
       an outer distal portion including (1) a lumen configured to receive the inner distal portion, and (2) a cavity adjacent to the lumen and housing a tissue removal tool, wherein the cavity and the tissue removal tool are positioned along a distal edge of the outer distal portion, and the inner lumen is external of the cavity;
    wherein the tissue removal tool is configured to sever tissue in response to the inner distal portion moving proximally relative to the outer distal portion and the tissue removal tool moving distally outward from the cavity.

15. The tissue removal device of claim 14, wherein the tissue removal tool is movable relative to portions of the outer distal portion proximate to the tissue removal tool.

16. The tissue removal device of claim 14, further comprising:
    a gap between an outer surface of the inner distal portion and an inner surface of the outer distal portion, wherein a radial width of the gap is greater at a first side of the inner distal portion having the at least one side port than at a second side of the inner distal portion opposite of the first side.

17. The tissue removal device of claim 14, wherein the tissue removal tool is movable from within the cavity in response to pushing the tissue removal tool of the outer distal portion.

18. The tissue removal device of claim 14, wherein the at least one side port of the inner distal portion is angled in a distal direction toward a distal end of the inner distal portion.

19. The tissue removal device of claim 14, wherein the tissue removal tool extends about a full circumference of the inner distal portion.

* * * * *